US008881899B2

(12) United States Patent
Fink et al.

(10) Patent No.: US 8,881,899 B2
(45) Date of Patent: *Nov. 11, 2014

(54) TRANSPARENT CATHETER SECUREMENT SYSTEM

(71) Applicant: Covidien LP, Mansfield, MA (US)

(72) Inventors: E. David Fink, Franklin, MA (US); Richard L. Fiser, Wildwood, MO (US); Bradley M. Anthony, Eaton, NY (US); William Brandon, Plainville, MA (US); David Hibbitt, Doncaster (GB)

(73) Assignee: Covidien LP, Mansfield, MA (US)

( * ) Notice: Subject to any disclaimer, the term of this patent is extended or adjusted under 35 U.S.C. 154(b) by 1 day.

This patent is subject to a terminal disclaimer.

(21) Appl. No.: 13/770,557

(22) Filed: Feb. 19, 2013

(65) Prior Publication Data

US 2013/0165864 A1    Jun. 27, 2013

Related U.S. Application Data

(63) Continuation of application No. 12/568,756, filed on Sep. 29, 2009, now Pat. No. 8,419,689.

(60) Provisional application No. 61/101,202, filed on Sep. 30, 2008.

(51) Int. Cl.
*A61M 5/32* (2006.01)
*B65D 83/10* (2006.01)
*A61M 25/02* (2006.01)

(52) U.S. Cl.
CPC ....... *A61M 25/02* (2013.01); *A61M 2025/0266* (2013.01)
USPC .......................................... 206/363; 604/180

(58) Field of Classification Search
USPC ........................... 604/174–180; 206/363–368
See application file for complete search history.

(56) References Cited

U.S. PATENT DOCUMENTS

| 4,224,937 A | 9/1980 | Gordon |
| 4,250,880 A | 2/1981 | Gordon |
| 4,397,647 A | 8/1983 | Gordon |
| 4,449,975 A | 5/1984 | Perry |
| 4,460,356 A | 7/1984 | Moseley |

(Continued)

FOREIGN PATENT DOCUMENTS

| WO | WO 98/15312 | 4/1998 |
| WO | WO 02/11786 A2 | 2/2002 |

OTHER PUBLICATIONS

International Search Report from counterpart International Application No. PCT/US2009/058910 filed Sep. 30, 2009.

(Continued)

*Primary Examiner* — Aarti B Berdichevsky
*Assistant Examiner* — Bradley Osinski

(57) ABSTRACT

A securement device for securing a catheter to a patient is provided. The securement device includes a base including a support member and at least one securement arm extending away from the support member. The support member defines a cradle portion, the cradle portion of the support member being configured to receive at least a portion of a catheter. The at least one securement arm being movable over the cradle portion to a position to secure a catheter within the cradle portion. The securement device further includes a cover member configured to be received over the base and dimensioned to secure the base to a patient.

4 Claims, 4 Drawing Sheets

(56) References Cited

U.S. PATENT DOCUMENTS

| | | |
|---|---|---|
| 4,490,141 A | 12/1984 | Lacko et al. |
| 4,563,177 A | 1/1986 | Kamen |
| 4,678,462 A | 7/1987 | Vaillancourt |
| 4,698,057 A | 10/1987 | Joishy |
| 4,737,143 A | 4/1988 | Russell |
| 4,826,486 A | 5/1989 | Palsrok |
| 4,863,432 A | 9/1989 | Kvalo |
| 4,976,698 A | 12/1990 | Stokley |
| 5,084,026 A | 1/1992 | Shapiro |
| 5,215,532 A | 6/1993 | Atkinson |
| 5,300,037 A | 4/1994 | Delk et al. |
| 5,306,256 A | 4/1994 | Jose |
| 5,314,411 A | 5/1994 | Bierman et al. |
| 5,344,415 A | 9/1994 | DeBusk |
| 5,354,282 A | 10/1994 | Bierman |
| 5,372,589 A | 12/1994 | Davis |
| 5,413,562 A | 5/1995 | Swauger |
| 5,685,859 A | 11/1997 | Kornerup |
| 5,810,781 A | 9/1998 | Bierman |
| 5,833,667 A | 11/1998 | Bierman |
| 5,885,254 A | 3/1999 | Matyas |
| 5,897,519 A | 4/1999 | Shesol et al. |
| 5,947,931 A | 9/1999 | Bierman |
| 6,113,577 A | 9/2000 | Hakky et al. |
| 6,231,548 B1 | 5/2001 | Bassett |
| 6,290,676 B1 | 9/2001 | Bierman |
| 6,302,867 B1 | 10/2001 | Brown, Jr. et al. |
| 6,428,515 B1 | 8/2002 | Bierman et al. |
| 6,582,403 B1 | 6/2003 | Bierman et al. |
| 6,673,046 B2 | 1/2004 | Bierman et al. |
| 7,014,627 B2 | 3/2006 | Bierman |
| 7,018,362 B2 | 3/2006 | Bierman et al. |
| 7,220,246 B2 | 5/2007 | Raulerson et al. |
| D547,862 S | 7/2007 | Dikeman et al. |
| 7,413,561 B2 | 8/2008 | Raulerson et al. |
| 8,419,689 B2 * | 4/2013 | Fink et al. .................. 604/180 |
| 2002/0188255 A1 | 12/2002 | Bierman et al. |
| 2005/0027258 A1 | 2/2005 | Bierman et al. |
| 2006/0129103 A1 | 6/2006 | Bierman et al. |
| 2006/0161109 A1 | 7/2006 | Huet |
| 2006/0264836 A1 | 11/2006 | Bierman |
| 2008/0065022 A1 | 3/2008 | Kyvik et al. |
| 2008/0097334 A1 | 4/2008 | Dikeman et al. |
| 2008/0171993 A1 | 7/2008 | Beran |
| 2008/0200880 A1 | 8/2008 | Kyvik et al. |
| 2009/0093769 A1 | 4/2009 | Wright et al. |

OTHER PUBLICATIONS

Extended European Search Report dated Feb. 21, 2012 from corresponding European Application No. EP 09818393.

Chinese Office Action dated Oct. 26, 2012, in copending Chinese Application No. 200980138766.

Chinese Office Action dated May 17, 2013, in copending Chinese Application No. 200980138766.

Australian Examination Report dated May 23, 2013 in copending Australian Application No. 2009298667.

* cited by examiner

TRANSPARENT CATHETER SECUREMENT SYSTEM

CROSS-REFERENCE TO RELATED APPLICATION

The present application is a continuation application of and claims the benefit of priority under 35 U.S.C. §120 to co-pending U.S. patent application Ser. No. 12/568,756, titled TRANSPARENT CATHETER SECUREMENT SYSTEM, which was filed on Sep. 29, 2009, which claims benefit to and priority from U.S. Provisional Application No. 61/101,202, filed Sep. 30, 2008, the entire content of each which is incorporated herein by reference for all purposes.

BACKGROUND

1. Technical Field

This present disclosure relates to a securement system for securing a catheter to a patient. More particularly, the present disclosure relates to a transparent securement system for securely supporting a catheter on a patient and protecting a catheterization site.

2. Background of Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical line properly positioned for the duration of treatment, the catheter or medical line may be secured to the patient in a variety of ways. Most commonly, this involves taping the catheter or medical line to the patient. Additionally, a transparent dressing is applied over a portion of the catheter or medical line to protect the catheterization site while enabling visual observation.

Securing a catheter with tape upon the patient traditionally is cumbersome and has certain drawbacks. The use of tape at the insertion site can retain dirt or other contaminant particles, potentially leading to infection of the patient. Tape also fails to limit catheter motion and, therefore, contributes to motion related complications like phlebitis, infiltration, and catheter migration. Additionally, removal of the tape can itself cause undesired motion of the catheter upon the patient.

Tape and transparent dressings also require periodic changes. The frequent, often daily, removal and reapplication of adhesive tape to the skin of the patient may excoriate the skin in the area around the dressing. Such repeated applications of tape over the catheter or medical line can additionally lead to the build up of adhesive residue on the outer surface of the catheter or medical line. This residue can result in contaminants adhering to the catheter itself, increasing the likelihood of infection of the insertion site. This residue may also make the catheter or medical line stickier and more difficult to handle for healthcare providers.

Accordingly, a need exists for an efficient system for securing a catheter to a patient that enables a clinician to monitor the catheter and catheter insertion site for infection, irritation and other associated complications.

SUMMARY

A securement device for securing a catheter to a patient is provided. The securement device includes a base including a support member and at least one securement arm extending away from the support member. The support member defines a cradle portion, the cradle portion of the support member being configured to receive at least a portion of a catheter. The at least one securement arm being movable over the cradle portion to a position to secure a catheter within the cradle portion. The securement device further includes a cover member configured to be received over the base and dimensioned to secure the base to a patient.

The at least one securement arm may include an adhesive surface. The adhesive surface may be protected by a release layer. The base may include two securement arms. A first securement arm may extend from the base in a first direction and a second securement arm may extend from the base in an opposite direction. The second securement arm may be axially offset from the first securement arm. The first and second securement arms may each be of a length sufficient to extend across the base to engage the skin of a patient. The at least one securement arm may include a first end secured to the base and a second end to engage a patient. The base may include an adhesive portion on a bottom surface thereof. At least one of the securement arms may include an opening configured to receive an access port formed on a catheter.

The cover member may be transparent. The cover member may define a substantially rectangular member. The cover member may include an opening configured to receive an access port formed on a catheter.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
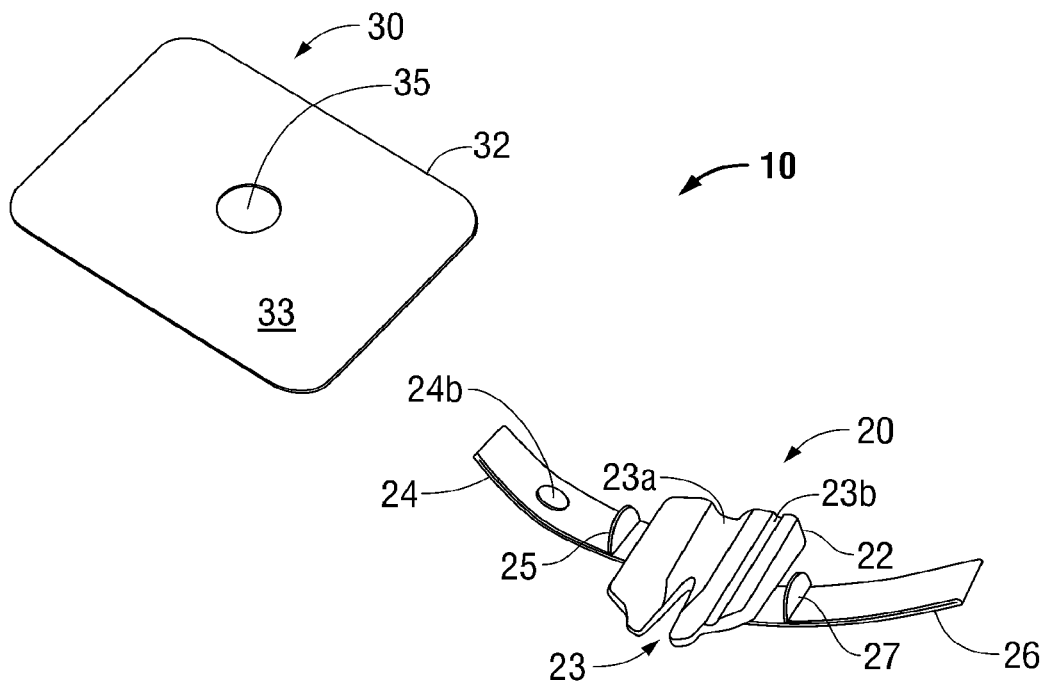
FIG. 1 is a perspective top view of an embodiment of the securement device of the present disclosure, including base member and cover.

The embodiments of the present disclosure will be shown with respect to catheter 5 (FIG. 2) having a cannula 5a and a hub 5b. Hub 5b further includes an access port 5c. Catheter 5 will be shown attached to a tube set 6 and with cannula 5a being received in a vein "V" of a hand of a patient "P". Catheter 5, tube set 6 and patient "P" are shown for illustrative purposes only. The aspects of the present disclosure should not be read as limited by catheter 5, tube set 6 and/or the location of cannula 5a of catheter 5 when introduced into the body.

With reference now to FIG. 1, a securement device according to the present disclosure is shown generally as securement device 10. Securement device 10 includes a base member 20 and a cover 30.

Figure 2:
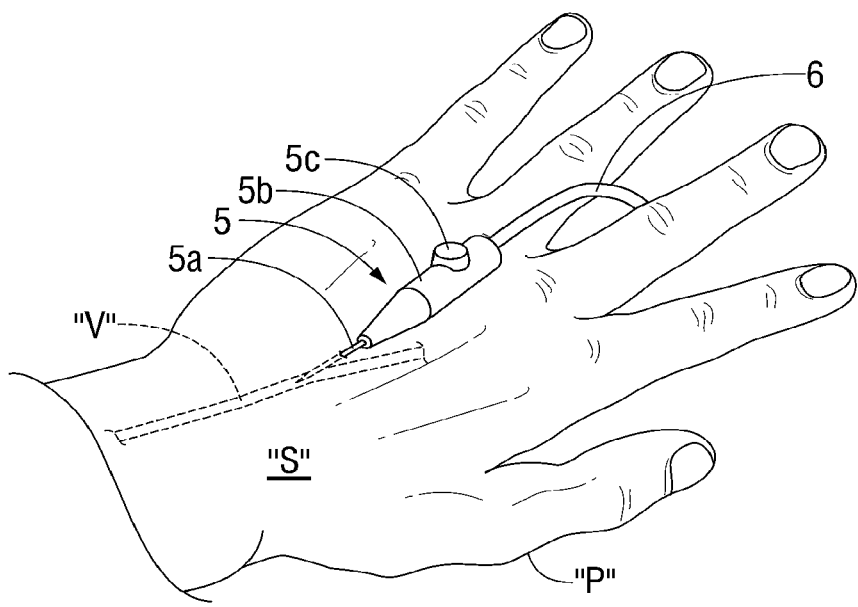
FIG. 2 is an illustration of a hand including a catheter engaging a vein.

Still referring to FIG. 1, base member 20 includes a semi-rigid support member 22 configured to support catheter 5 that has been received in a patient (FIG. 2). Support member 22 may be composed of foam or other suitable semi-rigid material. Support member 22 includes a substantially V-shaped slot 23 configured to be received about catheter 5 (FIG. 2). Support member 22 further includes a recessed or cradle portion 23a for supporting hub 5b of catheter 5 (FIG. 2). It is envisioned that support member 22 may have other suitable configurations to facilitate cradling of catheter 5. Support member 22 optionally includes a groove 23b extending along recessed portion 23a for selectively receiving tube set 6 (FIG. 2). Base member 20 of securement device 10 further includes a pair of securement arms 24, 26. First and second securement arms 24, 26 extend outwardly from V-shaped slot 23 and are of sufficient length and width to be folded over hub portion 5b of catheter 5 when catheter 5 is received in V-shaped slot 23 and cradle portion 23a. Securement arms 24, 26 may be integrally formed with base member 20. Alternatively, securement arms 24, 26 are secured to base member 20 using adhesive, glue, welding or other suitable means. In one embodiment, securement arms 24, 26 are formed from transparent plastic strips and may be of the same or different sizes and/or configurations. It is envisioned that base member 20 may include a single or multiple securement arms and that a variety of different materials of construction may be used.

With reference still to FIG. 1, first and second securement arms 24, 26 include respective first and second release layers 25, 27, respectively, for covering adhesive surfaces 24a, 26a (FIG. 4) of respective securement arms 24, 26. Adhesive surfaces 24a, 26a may be coated with adhesive, glue or other suitable material for releasably securing securement arms 24, 26 to the skin of a patient. Release layers 25, 27 protect adhesive surfaces 24a, 26a from incidental contact with a care provider, patient or other object until such time as securement arms 24, 26 are ready to be applied. In an alternative embodiment, securement arms 24, 26 may be coated with a substance (not shown) that remains tact-free until moistened or otherwise activated by a clinician. First securement arm 24 includes an opening 24b configured to receive access port 5c of catheter 5. Either or both of securement arms 24, 26 may include an opening to receive access port 5c. Optionally, the bottom surface (not shown) of base member 20 includes a third release layer (not shown) selectively covering an adhesive portion (not shown) of base member 20. In an alternative embodiment, package 50 (FIG. 8) may form the third release layer. The adhesive portion may include all or only part of the bottom surface of base member 20. As will be discussed in further detail below, the bottom surface of base member 20 is configured to adhere to skin "S" of a patient "P" and initially secure base member 20 thereto.

Figure 8:
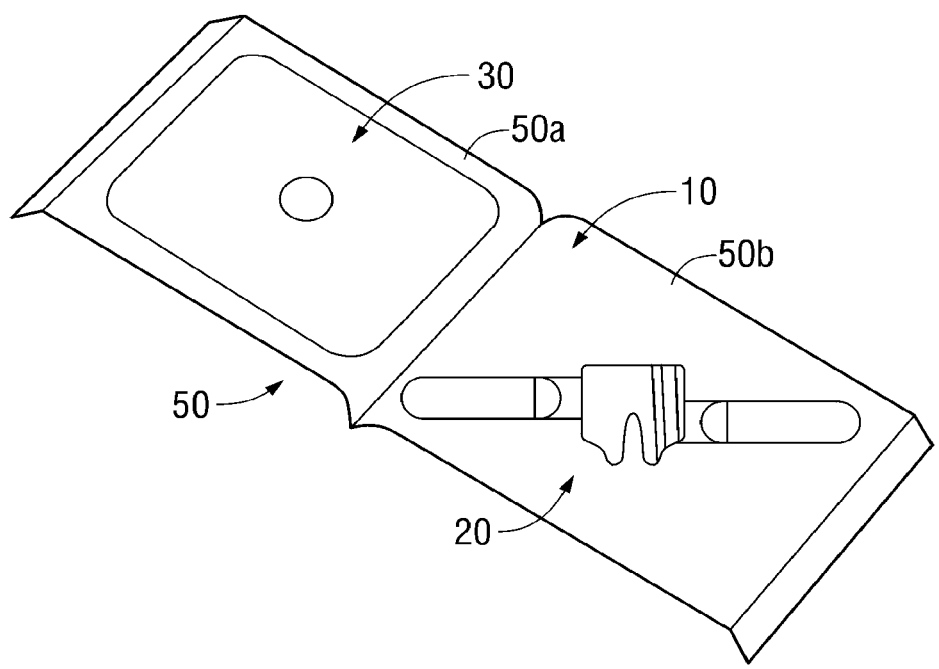

Still referring to FIG. 1, cover 30 defines a substantially rectangular cover member 32 sized and dimensioned to be received over base member 20 to secure first and second securement arms 24, 26 and catheter 5 to skin "S" of a patient "P" after securement arms 24, 26 have been secured about catheter 5. Alternative configurations of cover member 32 are envisioned, including circular, triangular and square. Cover member 32 includes a fourth release layer 33 selectively covering an adhesive portion (not shown) formed on bottom surface 32b (FIG. 6) of cover member 32. In an alternative embodiment, package 50 (FIG. 8) may form fourth release layer 33 (FIG. 8). Cover member 32 further includes an opening 35 configured to receive access port 5c of catheter 5 when cover member 32 is placed over catheter 5 (FIG. 2) after having been secured to base member 20.

Turning briefly to FIG. 8, one embodiment of securement device 10 is provided in package 50. Package 50 is formed from first and second sheets 50a, 50b. To access base member 20 and cover 30, a clinician separates first and second sheets 50a, 50b from one another to expose securement device 10. As discussed above, package 50 may form fourth release layer 33 for protecting the adhesive portion of cover member 32 and third release layer for protecting the adhesive portion of base member 20.

The application of securement device 10 will now be described with reference to FIGS. 2-5. Referring initially to FIG. 2, in preparation for using securement device 10, cannula 5a of catheter 5 is inserted into a patient's vein "V" (shown in phantom in FIG. 2) by a clinician (not shown) according to standard practice. Extension tubing set 6 is then connected to hub 5b of catheter 5.

Figure 3:
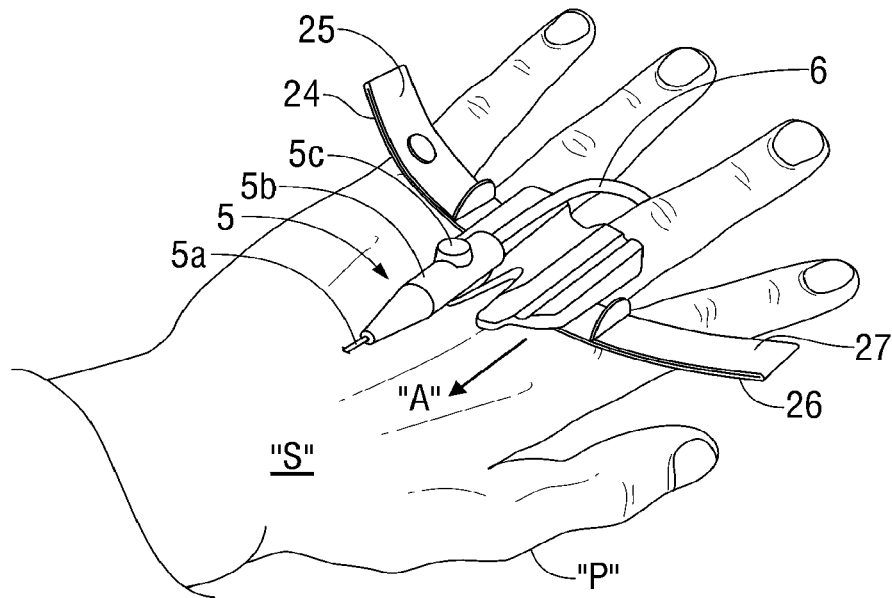
FIG. 3 is a perspective view of the base member of the securement device of FIG. 1 positioned about the catheter of FIG. 2.

With reference now to FIG. 3, catheter 5 is next held stationary by the clinician as slotted base member 20 of securement device 10 is placed along hub 5b of catheter 5, in the direction of arrow "A". In the case where bottom surface (not shown) of base member 20 includes an adhesive portion (not shown), the third release layer (not shown) is removed from the bottom surface of base member 20 prior to sliding slotted base member 20 about catheter 5. Alternatively, base member 20 is separated from its packaging to expose the adhesive portion. In this manner, base member 20 is at least partially adhered to the skin "S" prior to further securement by first and second securement arms 24, 26. Catheter 5 is positioned within V-shaped slot 23 and cradle portion 23a and is restrained from moving side-to side by support member 22. A portion of tube set 6 may then be received in groove 23b formed in base member 20 to secure tube set 6 to patient "P".

Figure 4:
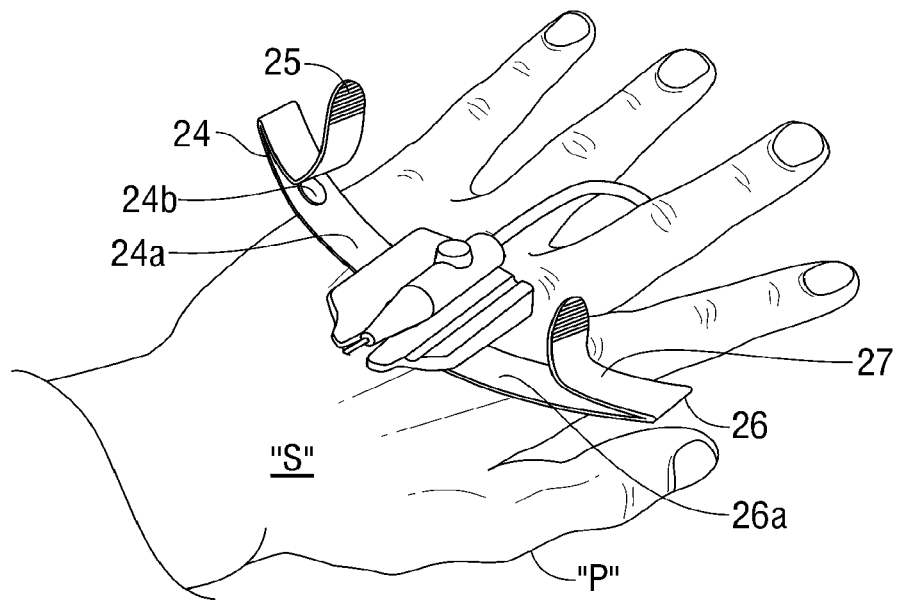
FIG. 4 is a perspective view of the base member of the securement device of FIG. 1 positioned about the catheter of FIG. 2.
Figure 5:
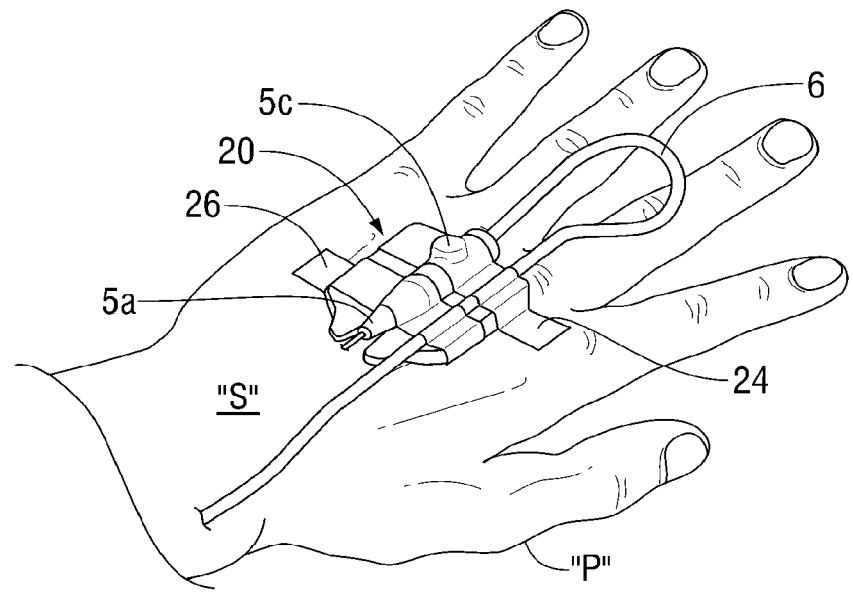
FIG. 5 is a perspective view of the catheter and base member of FIGS. 3 and 4, wherein the catheter is partially secured by the base member.

With reference to FIG. 4, once base member 20 of securement device 10 is adhered to skin "S", or at least base member 20 has been positioned about catheter 5 with hub 5b supported by support member 22 first release layer 25 on first securement arm 24 is removed to expose adhesive surfaces 24a. First securement arm 24 is then folded over catheter hub 5b to contain catheter 5 within recessed portion 23a of base member 20. Access port 5c of catheter 5 is received within opening 24b of first securement arm 24 to permit continued access to access port 5c. Depending on the length of first securement arm 24, first securement arm 24 may be adhered to base member 20 and/or skin "S" of patient "P". Second release layer 27 is then removed from second securement arm 26 to expose second adhesive surface 26a. Second securement arm 26 is then folded over catheter hub 5b to adhere second securement arm 26 to catheter hub 5b, and, optionally, adhere second securement arm 26 to base member 20 and/or skin "S".

Figure 6:
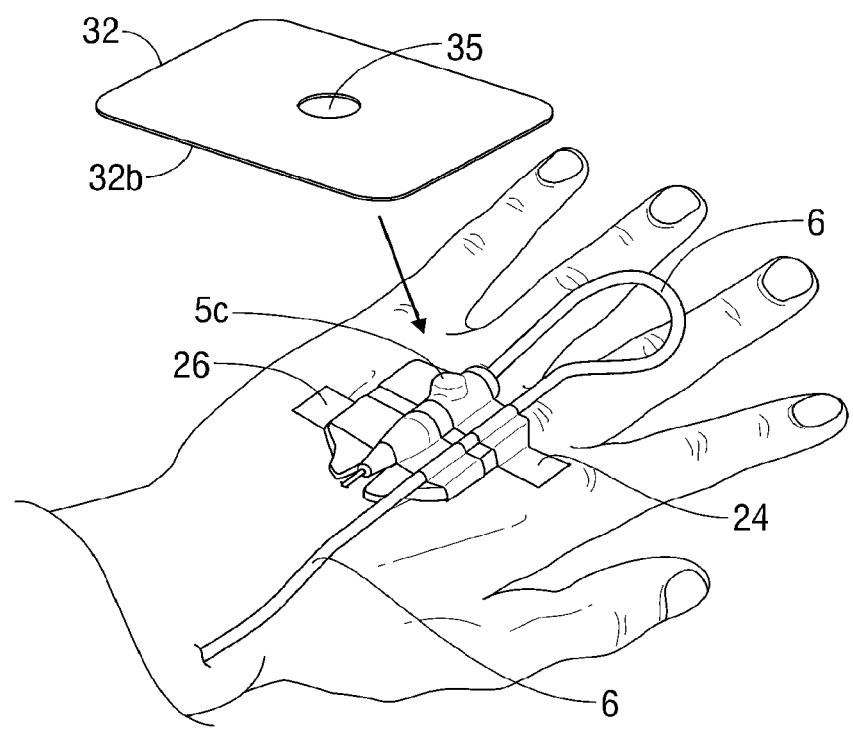
FIG. 6 is a perspective view of the catheter and securement device of FIGS. 3-5, wherein the cover member is being positioned over the catheter and base member.
Figure 7:
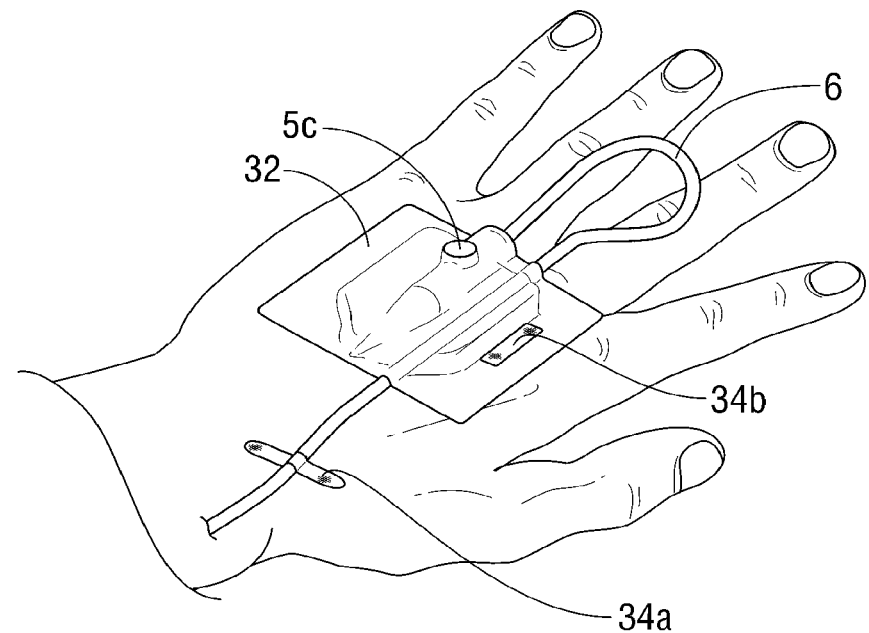
FIG. 7 is a perspective view of the catheter and securement device of FIG. 6, wherein the catheter is completely secured and covered by the securement device; and, FIG. 8 is a perspective view of the securement device of FIGS. 3-7 in packaging.

Next, referring to FIGS. 6 and 7, fourth release layer 33 is removed from bottom surface 32b of cover member 32 to expose the adhesive portion (not shown) formed on bottom surface 32b of cover member 32. Alternatively, cover member 32 is separated from package 50 (FIG. 8) to expose the adhesive portion. Cover member 32 is then applied about hub 5b to substantially cover hub 5b of catheter 5 and base member 20 of securement device 10 further securing catheter 5 in place. Cover member 32 provides a smooth outer surface for securement device 10. Top surface 32a of cover portion 32 may include, for example, a piece of tape 34a and/or label material 34b for taping down the extension tubing and/or recording clinical information. Furthermore, transparent cover member 32 permits visual observation of the catheterization site.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A method of facilitating securing a catheter to a patient comprising providing a securement device having a base including a support member and at least one securement arm extending away from the support member, the support member configured to receive at least a portion of the catheter and having an adhesive portion releasably adhered to a first package sheet for protecting the adhesive portion prior to securing the catheter to the patient; and a cover member configured to cover the base and having an adhesive portion and releasably adhered to a second package sheet for protecting the adhesive portion of the cover member prior to securing the catheter to the patient, wherein the first and second package sheets are joined together to enclose the securement device prior to use and are separable from one another to expose the securement device.

2. The method of claim 1, wherein the securement device has two securement arms.

3. The method of claim 1, wherein the support member has a cradle portion configured to receive the catheter and wherein the at least one securement arm is configured to be foldable over the cradle portion to secure the catheter within the base.

4. The method of claim 3, wherein the cover is configured to cover the at least one securement arm over the cradle portion.

* * * * *